US011547734B2

(12) United States Patent
Kalahasti et al.

(10) Patent No.: US 11,547,734 B2
(45) Date of Patent: Jan. 10, 2023

(54) TOPICAL MUSCLE RELAXATION COMPOSITIONS AND METHODS

(71) Applicant: MARY KAY INC., Addison, TX (US)

(72) Inventors: Geetha Kalahasti, Plano, TX (US); Shona Burkes-Henderson, Dallas, TX (US); David Gan, Southlake, TX (US)

(73) Assignee: MARY KAY INC., Addison, TX (US)

( * ) Notice: Subject to any disclaimer, the term of this patent is extended or adjusted under 35 U.S.C. 154(b) by 0 days.

(21) Appl. No.: 16/457,027

(22) Filed: Jun. 28, 2019

(65) Prior Publication Data

US 2020/0009209 A1 Jan. 9, 2020

Related U.S. Application Data

(60) Provisional application No. 62/693,545, filed on Jul. 3, 2018.

(51) Int. Cl.
*A61K 36/53* (2006.01)
*A61K 8/9789* (2017.01)
*A61P 17/00* (2006.01)
*A61Q 19/08* (2006.01)
*A61K 9/107* (2006.01)
*A61K 9/06* (2006.01)
*A61K 8/04* (2006.01)
*A61K 8/06* (2006.01)
*A61K 9/00* (2006.01)

(52) U.S. Cl.
CPC .............. *A61K 36/53* (2013.01); *A61K 8/042* (2013.01); *A61K 8/064* (2013.01); *A61K 8/9789* (2017.08); *A61K 9/0014* (2013.01); *A61K 9/06* (2013.01); *A61K 9/107* (2013.01); *A61P 17/00* (2018.01); *A61Q 19/08* (2013.01); *A61K 2800/10* (2013.01)

(58) Field of Classification Search
CPC ....................................................... A61Q 9/08
See application file for complete search history.

(56) References Cited

U.S. PATENT DOCUMENTS

| | | | |
|---|---|---|---|
| 2,798,053 A | 7/1957 | Brown | |
| 3,755,560 A | 8/1973 | Dickert et al. | |
| 4,421,769 A | 12/1983 | Dixon et al. | |
| 4,509,949 A | 4/1985 | Huang et al. | |
| 4,599,379 A | 7/1986 | Flesher et al. | |
| 4,628,078 A | 12/1986 | Glover et al. | |
| 4,835,206 A | 5/1989 | Farrar et al. | |
| 4,849,484 A | 7/1989 | Heard | |
| 5,011,681 A | 4/1991 | Ciotti et al. | |
| 5,087,445 A | 2/1992 | Haffey et al. | |
| 5,100,660 A | 3/1992 | Hawe et al. | |
| 7,531,193 B2 | 5/2009 | Demarne et al. | |
| 7,566,464 B2 | 7/2009 | Belfer | |
| 7,758,878 B2 | 7/2010 | Scimeca et al. | |
| 7,959,953 B2 | 6/2011 | Zimmerman et al. | |
| 8,025,907 B2 | 9/2011 | Belfer | |
| 8,168,211 B2 | 5/2012 | Dumas et al. | |
| 2004/0109905 A1 | 6/2004 | Bagchi | |
| 2004/0115163 A1 | 6/2004 | Gedouin et al. | |
| 2005/0163880 A1 | 7/2005 | Pusateri et al. | |
| 2007/0041922 A1 | 2/2007 | Reinhart et al. | |
| 2007/0048245 A1 | 3/2007 | Belfer | |
| 2008/0003311 A1* | 1/2008 | Breton | A61Q 19/08 424/745 |
| 2010/0324152 A1* | 12/2010 | Schmaus | A61Q 19/10 514/738 |
| 2013/0315846 A1 | 11/2013 | Collier et al. | |
| 2014/0066837 A1* | 3/2014 | Moy | A61M 37/0092 424/94.1 |
| 2014/0275289 A1* | 9/2014 | Weisman | C08K 5/01 514/772.6 |
| 2015/0150922 A1 | 6/2015 | Hefti | |
| 2018/0055904 A1* | 3/2018 | Lavaud | A61K 36/88 |

FOREIGN PATENT DOCUMENTS

| | | | |
|---|---|---|---|
| CN | 103635200 | 3/2014 | |
| CN | 105476892 A * | 4/2016 | |
| CN | 105816392 | 8/2016 | |
| EP | 1776087 | 4/2007 | |
| EP | 2275078 | 1/2011 | |
| FR | 2868307 A1 * | 10/2005 | ........... A61K 8/9789 |
| JP | 2008013437 | 1/2008 | |
| JP | 2009249306 | 10/2009 | |
| JP | 5518297 | 6/2014 | |

(Continued)

OTHER PUBLICATIONS

Personal Care Product guide, Mar. 22, 2017, Gattefosse.*
International Search Report and Written Opinion issued in counterpart Application No. PCT/US2019/039854, dated Oct. 22, 2019.
CTFA, International Cosmetic Ingredient Dictionary and Handbook, 12th Ed., 2008, pp. 41, 1443, and 2393-2395.
Nature's Way, CamoCare Organics, Youth Elixir Serum, Intense Anti-Wrinkle, 1 fl oz (30 ml) (Discontinued Item). Retrieved Oct. 12, 2017, from https://www.iherb.com/pr/nature-s-way-camocare-organics-youth-elixir-serum-intense-anti-wrinkle-1-fl-oz-30-ml/11188.

(Continued)

*Primary Examiner* — Gina C Justice
(74) *Attorney, Agent, or Firm* — Norton Rose Fulbright US LLP

(57) ABSTRACT

A method for reducing muscle contraction of a facial muscle or reducing the appearance of a fine line or wrinkle is disclosed. The method can include topical application of a composition to facial skin and/or to the fine line or wrinkle. The composition can include an effective amount of *Rosmarinus officinalis* leaf extract, an effective amount of *Lavendula stoechas* extract, and an effective amount of *Acmella oleracea* extract. Topical application of the composition to facial skin can reduce muscle contraction of the facial muscle. Topical application of the composition to the fine line or wrinkle can reduce the appearance of the fine line or wrinkle.

16 Claims, 5 Drawing Sheets

(56) References Cited

FOREIGN PATENT DOCUMENTS

| KR | 20180027664 | | 3/2018 |
|---|---|---|---|
| KR | 20180027664 A | * | 3/2018 |
| WO | WO 2006/018198 | | 2/2006 |

OTHER PUBLICATIONS

Hou, Yuankai. *How to Construct Leisure Agriculture*. Huazhong University of Science & Technology Press, 2017 (English abstract provided).

Office Action issued in Corresponding Chinese Application No. 201980057216.2, dated Oct. 11, 2021 (English Translation provided).

Search Report issued in Corresponding Chinese Application No. 201980057216.2, dated Sep. 28, 2021 (English Translation provided).

Database GNPD [Online] MINTEL, "Anti-Aging Serum Maximum Repair", retrieved from URL < www.gnpd.com > database accession No. 2802613, Jan. 29, 2015.

Database GNPD [Online] MINTEL, "Anti-Wrinkle Eye Serum Cream of Jing Cheng", retrieved from URL < www.gnpd.com > database accession No. 4007209, May 17, 2016.

Database GNPD [Online] MINTEL, "Hair Repair & Treatment Oil", retrieved from URL < www.gnpd.com > database accession No. 5560845, Apr. 23, 2018.

Database GNPD [Online] MINTEL, "Soothing Anti-Aging Cream", retrieved from URL < www.gnpd.com > database accession No. 4521023, Feb. 14, 2017.

Extended European Search Report issued in Corresponding European Application No. 19830360.4, dated Mar. 21, 2022.

* cited by examiner

\* p<0.05 for mean response relative to baseline

* p<0.05 for mean score relative to baseline

* p<0.05 for mean score relative to baseline

TOPICAL MUSCLE RELAXATION COMPOSITIONS AND METHODS

CROSS-REFERENCE TO RELATED APPLICATIONS

The present application claims priority to U.S. provisional patent application 62/693,545 filed Jul. 3, 2018, the disclosure of which is hereby incorporated by reference in its entirety.

BACKGROUND OF THE INVENTION

A. Field of the Invention

The present invention relates generally to a composition that can be used to relax facial muscles and/or reduce the appearance of fine lines or wrinkles. The composition can include a combination of plant-based extracts such as *Rosmarinus officinalis* leaf extract, *Lavendula stoechas* extract, and *Acmella oleracea* extract.

B. Background

Certain types of wrinkles develop over time on facial skin due to repetitive muscle contraction. These types of wrinkles are typically referred to as rhytides, examples of which can include frown or glabellar lines, forehead lines, crow's feet, bunny or nasalis lines, dimpled chin, smile lift lines, lip lines, etc. Currently, a wide variety of commercially available treatment materials are available and are purportedly effective as facial muscle relaxants/muscle contraction suppressants. These materials are said to be capable of reducing the appearance of such wrinkles. Non-limiting examples of such treatment materials include injectable neuromodulators such as Botox® (onabotulinumtoxinA), Dysport® (abobotulinumtoxinA), or Xeomin® (incobotulinumtoxinA). Other examples include topically administered treatment materials such as chemical compounds (e.g., gamma-aminobutyric-acid) and peptides (e.g., acetyl hexapeptide-3).

Various problems are associated with injectable neuromodulators, such as allergic reactions, rash, itching, injection site reactions (bruising, bleeding, pain, redness, swelling, or tenderness), muscle stiffness, fever, cough, sore throat, flu-like symptoms, neck or back pain, and the potential to spread from the injection site to other parts of the body, resulting in serious risks including difficulty talking, swallowing or breathing, muscle weakness, drooping eyelids, and blurred or double vision. Similarly, chemical compounds have their own drawbacks such as skin irritation and potential allergic reactions. Aside from the physiological problems associated with injectable neuromodulators and chemical compounds, these elective cosmetic procedures can be cost-prohibitive for a large segment of the population who may benefit.

There have been a few attempts to produce natural-based ingredients that have the ability to relax facial muscles. One such attempt is the development of *Acmella oleracea* extracts. While these extracts may offer some muscle relaxation effect, the effect may not be sufficient to effectively relax facial muscles and reduce the appearance of fine lines or wrinkles.

Thus, previous attempts to improve the visual appearance of skin have been shown to have various drawbacks such as high costs, medical risks, skin irritation, prolonged recovery periods, or inefficient delivery of the promised skin benefits.

SUMMARY OF THE INVENTION

The inventors have identified a solution to at least some of the problems associated with treating fine lines or wrinkles. The solution resides in a combination of plant-based ingredients that is effective at reducing muscle contraction of facial muscles. In one particular aspect, the facial muscle contraction can be reduced by reducing contraction of myotubes via reducing an influx of calcium levels in the myotubes. Reducing the influx of calcium levels in the myotubes can reduce or inhibit an action potential in the myotubes, thus reducing or preventing muscle contraction. This combination of ingredients also has the ability to modulate biochemical pathways that can further help reduce the appearance of fine lines or wrinkles such as by stimulating collagen production in skin (e.g., keratinocytes or human dermal fibroblasts) and/or reducing enzymatic activity or production of enzymes associated with the degradation of extracellular matrix proteins (e.g., matrix metalloproteinase (MMP) enzymes such as MMP-1, MMP3, and/or MMP-9). Still further, the combination of ingredients also has the ability to increase collagen expression and laminin production in skin cells (e.g., keratinocytes or human dermal fibroblasts). The combination of the plant-based ingredients include at least two of or all three of *Rosmarinus officinalis* leaf extract, *Lavendula stoechas* extract, and/or *Acmella oleracea* extract. This combination of plant-based ingredients can be used to create topical skin compositions that reduce the appearance of and/or prevent the formation of fine lines or wrinkles, including deep facial line wrinkles or rhytides that can be linked to repetitive facial muscle contraction over prolonged periods of time (e.g., 1, 2, 4, 6, 8, 12, or more months or several years). Notably, the combination of ingredients can be used to reduce the appearance of and/or prevent the formation of both static and dynamic fine lines or wrinkles.

In one aspect of the present invention, there is disclosed a method for reducing muscle contraction of a facial muscle in a person. In another aspect, there is disclosed a method for reducing the appearance of a fine line or wrinkle on a person's skin. The method can include topically applying to skin a composition comprising: (a) an effective amount of *Rosmarinus officinalis* leaf extract; (b) an effective amount of *Lavendula stoechas* extract; and/or (c) an effective amount of *Acmella oleracea* extract, wherein topical application of the composition to facial skin reduces muscle contraction of the facial muscle or wherein topical application of the composition to skin reduces the appearance of fine lines or wrinkles on a person's skin. Additionally, or alternatively, topical application can include rolling a microroller across the person's skin to increase penetration of the composition into the skin. In certain aspects, the composition includes *Rosmarinus officinalis* leaf extract and *Lavendula stoechas* extract, *Rosmarinus officinalis* leaf extract and *Acmella oleracea* extract, *Lavendula stoechas* extract and *Acmella oleracea* extract, or all of *Rosmarinus officinalis* leaf extract, *Lavendula stoechas* extract and *Acmella oleracea* extract. In certain aspects, facial muscle(s) that is/are contracted can be positioned directly under the skin where the composition is applied. In other aspects, facial muscle(s) that is/are contracted can be in close proximity to the skin but not directly underneath the skin where the composition is applied (e.g., within 3 centimeters, preferably with 2.5 cm, or more preferably within 2 cm, or even more preferably within 1.5 or 1 cm of the area of the skin that the composition has been applied to). The facial muscle can be a glabellar complex muscle, an orbicularis oculi muscle, a depressor muscle, or a *frontalis* muscle, or any combination thereof. Alternatively, the composition can be applied to non-facial skin (e.g., hands, thighs, neck, buttocks, décolleté region, feet, etc.) and can lead to reduced muscle contraction of muscles directly under the skin where the composition has been applied or in close proximity to the skin but not directly underneath the skin. In instances where the composition is applied to a fine line or wrinkle, the fine line or wrinkle can be a rhytide, and reduction in muscle contraction of the facial muscle reduces the appearance of the rhytide. In other instances, the fine line or wrinkle is not a rhytide.

The extracts used in the compositions of the present invention can each individually be obtained from water as an extracting solvent (e.g., aqueous extract), alcohol as an extracting solvent (e.g., alcohol extract), or a polyol as the extracting solvent (e.g., polyol extract), or any combinations of such extracting solvents (e.g., aqueous-alcoholic extract, aqueous-polyol extract, alcohol-polyol extract or aqueous-alcoholic-polyol extract). Non-limiting examples of alcohols can be methanol, ethanol, propanol, butanol, petnanol, hexanol, heptanol, octanol, etc. Non-limiting examples of polyols can be ethylene glycol, propylene glycol, glycerol, erythritol, xylitol, mannitol, volemitol, etc. Additionally, other extracting solvents can be used such as additional hydrophilic solvents or lipophilic solvents (e.g., methane, ethane, butane, propane, hexane, heptane, octane, dimethyl sulfoxide (DMSO), N-methyl-2-pyrrolidone (NMP), carbon dioxide such as use of carbon dioxide ($CO_2$) in supercritical extraction techniques). $CO_2$ supercritical extraction can include filling a column with ground dried plant material and pumping supercritical liquid carbon dioxide though the column at very high pressure (200-400 Bar), and then collecting the resulting extract.

In a preferred instance, the *Rosmarinus* officinalis leaf extract can be obtained from the leaf of *Rosmarinus* officinalis. The leaf can be subjected to a eutectigenesis extraction process using a fluid extraction mixture comprising betaine or hydrated betaine, a hydrogen bond donor compound (e.g., polyols, organic acids, etc.), and water. The eutectic extract can then be used in the compositions of the present invention. In some preferred instances, the hydrogen bond donor is an organic acid, preferably lactic acid. Eutectigenesis utilizes eutectic solvents which are mixtures of compounds having melting points lower than those of their constituents taken in isolation. In another preferred instance, the *Lavendula* stoechas extract is from a combination of the flower, leaf, and stem portions of *Lavendula* stoechas, and the extract can be prepared by subjecting these portions to a supercritical extraction process using carbon dioxide ($CO_2$) as the solvent. The supercritical $CO_2$ extract of *Lavendula* stoechas flower, leaf, and stem (flower/leaf/stem) can then be used in the compositions of the present invention. The $CO_2$ supercritical extract of the *Lavendula* stoechas flower/leaf/stem can also be mixed with caprylic/capric triglycerides and then used in the compositions of the present invention. In still another preferred instance, the *Acmella* oleracea extract is from the combination of the flower, leaf, and stem portions of *Acmella* oleracea, and the extract can be prepared by subjecting these portions (flower/leaf/stem) to a hydro-alcoholic (preferably hydro-ethanolic) extraction process or a hydro-alcoholic-polyol extraction process. The polyol in preferred instances can be 1,3-propanediol. The alcohol can be removed from the resulting extract. The *Acmella oleracea* extract can be then be used in the compositions of the present invention. Thus, in a preferred instance, the *Rosmarinus officinalis* leaf eutectic extract, the *Lavendula stoechas* flower/leaf/stem supercritical $CO_2$ extract, and the *Acmella oleracea* flower/leaf/stem hydro-alcohol-polyol extract can be used in the compositions and methods of the present invention.

An effective amount of *Rosmarinus officinalis* leaf extract in the composition can be 0.00001 to 25% w/w or any range therein (e.g., 0.00001 to 10% w/w, 0.00001 to 5% w/w, 0.00001 to 2% w/w, 0.00001 to 1% w/w, 0.00001 to 0.5% w/w, or 0.001 to 1% w/w, 0.01 to 1% w/w, 0.1 to 1% w/w. or 0.001 to 2% w/w, 0.01 to 2% w/w, or 0.1 to 2% w/w). An effective amount of *Lavendula stoechas* extract in the composition can be 0.00001 to 25% w/w or any range therein (e.g., 0.00001 to 10% w/w, 0.00001 to 5% w/w, 0.00001 to 2% w/w, 0.00001 to 1% w/w, 0.00001 to 0.5% w/w, or 0.001 to 1% w/w, 0.01 to 1% w/w, 0.1 to 1% w/w. or 0.001 to 2% w/w, 0.01 to 2% w/w, or 0.1 to 2% w/w). An effective amount of *Acmella* oleracea extract in the composition can be 0.00001 to 25% w/w or any range therein (e.g., 0.00001 to 10% w/w, 0.00001 to 5% w/w, 0.00001 to 2% w/w, 0.00001 to 1% w/w, 0.00001 to 0.5% w/w, or 0.001 tot % w/w, 0.01 to 1% w/w, 0.1 to 1% w/w. or 0.001 to 2% w/w, 0.01 to 2% w/w, or 0.1 to 2% w/w).

The compositions of the present invention can reduce contraction of myotubes. This can be done by reducing the influx of calcium into the myotubes, which can reduce or prevent an action potential from occurring in the myotubes. By reducing or preventing action potential development, contraction of the myotubes can be reduced or prevented. Notably, each of *Rosmarinus officinalis* leaf or an extract thereof, *Lavendula stoechas* or an extract thereof, and/or *Acmella oleracea* or an extract thereof has been shown by the inventors to reduce or prevent an influx of calcium into myotubes and to reduce or prevent muscle contraction. The compositions of the present invention can also stimulate collagen production in skin cells (e.g., keratinocytes and/or human dermal fibroblasts). In particular, it was discovered in the context of the present invention that *Acmella oleracea* or an extract thereof can increase collagen production in skin cells. The compositions of the present invention can also stimulate laminin production in skin cells (e.g., keratinocytes and/or human dermal fibroblasts). In particular, it was discovered in the context of the present invention that *Acmella oleracea* or an extract thereof can increase laminin production in skin cells. The compositions of the present invention can also reduce or inhibit matrix metalloproteinases (MMP) 1, 3, and 9 activity or production in skin cells (e.g., keratinocytes and/or human dermal fibroblasts). In particular, it was discovered in the context of the present invention that the *Rosmarinus officinalis* leaf or an extract thereof can reduce or inhibit each of MMP-1, MMP-3, and MMP-9 activity or production in skin cells. The skin can be facial skin such as skin located on a person's forehead, cheeks, chin, orbital area region (e.g., under the eyes, adjacent to the eyes such as where crow's feet form, eyelid, etc.). In certain preferred aspects, the facial skin is forehead skin or orbital area region skin, especially where crow's feet develop. Still further, the compositions of the present invention can be used to increase skin firmness, which can aid in reducing the appearance of loos, sagging, and/or flaccid skin.

In addition to *Rosmarinus officinalis* leaf or an extract thereof, *Lavendula stoechas* or an extract thereof, and/or *Acmella oleracea* or an extract thereof, the topical skin compositions of the present invention can further comprise one or more ingredients described herein. For example, the composition can comprise one or more additional ingredients selected from one or more cosmetic ingredients or pharmaceutical ingredients. In some instances, the compositions can include one or more conditioning agents, moisturizing agents, pH adjusters, structuring agents, silicone containing compounds, inorganic salts, and/or preservatives. In some aspects, the topical composition further includes water, preferably at least 50, 60, 70, 80, or 90, or more wt. % water, more preferably between 50 to 90 wt. % water. In some aspects, the topical compositions of the present invention may exclude one or more additional ingredients selected from one or more cosmetic ingredients or pharmaceutical ingredients. In still some particular aspects, the compositions of the present invention may exclude one or more of *Rosmarinus* officinalis leaf extract, *Lavendula stoechas* extract, and *Acmella oleracea* extract. In some aspects, the topical composition excludes water. In some aspects, the topical composition herein may be anhydrous or substantially anhydrous.

In particular aspects, the compositions of the present invention are formulated as a topical skin composition. The composition can have a dermatologically acceptable vehicle or carrier for the compounds and extracts. The composition can further include a moisturizing agent or a humectant, a surfactant, a silicone containing compounds, a UV agent, an oil, and/or other ingredients identified in this specification or those known in the art. The composition can be a mask, lotion, cream, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include sodium benzoate, iodopropynyl butylcarbamate, methylparaben, propylparaben, or a mixture of methylparaben and propylparaben. In some embodiments, the composition is paraben-free.

Compositions of the present invention can have UVA and UVB absorption properties. The compositions can have a sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a foundation, a night cream, a lipstick, a cleanser, a cleansing balm, a toner, a sunscreen, a mask, an anti-aging product, a deodorant, an antiperspirant, a perfume, a cologne, etc.

Also disclosed are the following Embodiments 1 to 40 of the present invention. Embodiment 1 is a method for reducing muscle contraction of a facial muscle in a person, the method comprising topically applying to facial skin a composition comprising: (a) an effective amount of *Rosmarinus officinalis* leaf extract; (b) an effective amount of *Lavendula stoechas* extract; and (c) an effective amount of *Acmella oleracea* extract, wherein topical application of the composition to the facial skin reduces muscle contraction of the facial muscle. Embodiment 2 is the method of claim 1, wherein the composition is applied to a fine line or wrinkle, and wherein the appearance of the fine line or wrinkle is reduced after topical application. Embodiment 3 is the method of claim 2, wherein the fine line or wrinkle is a rhytide, and wherein the reduction in muscle contraction of the facial muscle reduces the appearance of the rhytide. Embodiment 4 is the method of any one of Embodiments 1 to 3, wherein the facial muscle is a glabellar complex muscle, an orbicularis oculi muscle, a depressor muscle, or a frontalis muscle, or any combination thereof. Embodiment 5 is the method of any one of Embodiments 1 to 4, wherein each of the extracts is individually an aqueous extract, an alcohol extract, a polyol extract, or a combination thereof. Embodiment 6 is the method of any one of Embodiments 1 to 5, wherein: the *Rosmarinus officinalis* leaf extract is obtained with a fluid extraction solvent mixture comprising betaine, lactic acid, and water; the *Lavendula stoechas* extract is a *Lavendula stoechas* flower/leaf/stem extract obtained with a supercritical carbon dioxide ($CO_2$) extraction solvent; and the *Acmella oleracea* extract is obtained with a fluid extraction solvent mixture comprising water, ethanol, and 1,3 propanediol. Embodiment 7 is the method of any of Embodiments 1 to 6, wherein the composition comprises: 0.00001 to 10% w/w of *Rosmarinus* officinalis leaf extract; 0.00001 to 10% w/w of *Lavendula stoechas* extract; and, 0.00001 to 10% w/w of *Acmella oleracea* extract. Embodiment 8 is the method of any of Embodiments 1 to 7, wherein: the *Rosmarinus officinalis* leaf extract reduces an influx of calcium in the facial muscle and reduces the occurrence of an action potential in the facial muscle; the *Lavendula stoechas* extract reduces an influx of calcium in the facial muscle and reduces the occurrence of an action potential in the facial muscle; and the *Acmella oleracea* extract reduces an influx of calcium in the facial muscle and reduces the occurrence of an action potential in the facial muscle. Embodiment 9 is the method of any one of Embodiments 1 to 8, wherein the *Acmella oleracea* extract stimulates collagen production and laminin production in the skin. Embodiment 10 is the method of any one of Embodiments 1 to 9, wherein the *Rosmarinus officinalis* leaf extract reduces matrix metalloproteinases 1, 3, or 9 production in the skin. Embodiment 11 is the method of any one of Embodiments 1 to 10, wherein the facial skin is forehead skin, cheek skin, chin skin, or orbital area skin. Embodiment 12 is the method of Embodiment 11, wherein the skin is forehead skin. Embodiment 13 is the method of Embodiment 11, wherein the skin is orbital area skin. Embodiment 14 is the method of any of Embodiments 1 to 13, wherein the composition is an emulsion. Embodiment 15 is the method of Embodiment 14, wherein the emulsion is an oil-in-water emulsion. Embodiment 16 is the method of any one of Embodiments 1 to 13, wherein the composition is a gel. Embodiment 17 is a method of reducing the appearance of a fine line or wrinkle on a person's skin, the method comprising topically applying to the fine line or wrinkle a composition comprising: (a) an effective amount of *Rosmarinus officinalis* leaf extract; (b) an effective amount of *Lavendula stoechas* extract; and (c) an effective amount of *Acmella oleracea* extract, wherein topical application reduces the appearance of the fine line or wrinkle. Embodiment 18 is the method of Embodiment 17, wherein the composition reduces muscle contraction of a muscle that causes the appearance of the fine line or wrinkle when the muscle is contracted. Embodiment 19 is the method of any one of Embodiments 17 to 18, wherein the muscle is a glabellar complex muscle, an orbicularis oculi muscle, a depressor muscle, or a frontalis muscle, or any combination thereof. Embodiment 20 is the method of any one of Embodiments 17 to 19, wherein the fine line or wrinkle is a rhytide. Embodiment 21 is the method of any one of Embodiments 17 to 20, wherein each of the extracts is individually an aqueous extract, an alcohol extract, a polyol extract, or a combination thereof. Embodiment 22 is the method of any one of Embodiments 17 to 21, wherein: the *Rosmarinus* officinalis leaf extract is obtained with a fluid extraction solvent mixture comprising betaine, lactic acid, and water; the *Lavendula stoechas* extract is a *Lavendula stoechas* flower/leaf/stem extract obtained with a supercritical carbon dioxide ($CO_2$) extraction solvent; and the *Acmella* oleracea extract is obtained with a fluid extraction solvent mixture comprising water, ethanol, and 1,3 propanediol. Embodiment 23 is the method of any of Embodiments 17 to 22, wherein the composition comprises: 0.00001 to 10% w/w of *Rosmarinus officinalis* leaf extract; 0.00001 to 10% w/w of *Lavendula stoechas* extract; and, 0.00001 to 10% w/w of *Acmella oleracea* extract. Embodiment 24 is the method of any of Embodiments 17 to 23, wherein: the *Rosmarinus* officinalis leaf extract reduces an influx of calcium in the facial muscle and reduces the occurrence of an action potential in the facial muscle; the *Lavendula stoechas* extract reduces an influx of calcium in the facial muscle and reduces the occurrence of an action potential in the facial muscle; and the *Acmella oleracea* extract reduces an influx of calcium in the facial muscle and reduces the occurrence of an action potential in the facial muscle. Embodiment 25 is the method of any one of Embodiments 17 to 24, wherein the *Acmella oleracea* extract stimulates collagen production and laminin production in the skin. Embodiment 26 is the method of any one of Embodiments 17 to 25, wherein the *Rosmarinus officinalis* leaf extract reduces matrix metalloproteinases 1, 3, or 9 production in the skin. Embodiment 27 is the method of any one of Embodiments 17 to 26, wherein the person's skin is facial skin, preferably forehead skin, cheek skin, chin skin, or orbital area skin. Embodiment 28 is the method of Embodiment 27, wherein the skin is forehead skin. Embodiment 29 is the method of Embodiment 27, wherein the skin is orbital area skin. Embodiment 30 is the method of any of Embodiments 17 to 29, wherein the composition is an emulsion. Embodiment 31 is the method of Embodiment 30, wherein the emulsion is an oil-in-water emulsion. Embodiment 32 is the method of any one of Embodiments 17 to 31, wherein the composition is a gel. Embodiment 33 is a topical skin composition comprising: (a) an effective amount of *Rosmarinus officinalis* leaf extract; (b) an effective amount of *Lavendula stoechas* extract; and (c) an effective amount of *Acmella oleracea* extract, wherein the topical skin composition is capable of reducing the appearance of a fine line or wrinkle in a person's skin and/or is capable of reducing muscle contraction of a facial muscle in a person. Embodiment 34 is the composition of Embodiment 33, wherein each of the extracts is individually an aqueous extract, an alcohol extract, a polyol extract, or a combination thereof. Embodiment 35 is the composition of any one of Embodiments 33 to 34, wherein: the *Rosmarinus officinalis* leaf extract is obtained with a fluid extraction solvent mixture comprising betaine, lactic acid, and water; the *Lavendula stoechas* extract is a *Lavendula stoechas* flower/leaf/stem extract obtained with a supercritical carbon dioxide ($CO_2$) extraction solvent; and the *Acmella oleracea* extract is obtained with a fluid extraction solvent mixture comprising water, ethanol, and 1,3 propanediol. Embodiment 36 is the composition of any one of Embodiment 33 to 35, wherein the composition comprises: 0.00001 to 10% w/w of *Rosmarinus officinalis* leaf extract; 0.00001 to 10% w/w of *Lavendula stoechas* extract; and, 0.00001 to 10% w/w of *Acmella oleracea* extract. Embodiment 37 is the composition of any one of Embodiments 33 to 36, wherein: the *Rosmarinus officinalis* leaf extract is capable of reducing an influx of calcium in the facial muscle and reduces the occurrence of an action potential in the facial muscle; the *Lavendula stoechas* extract is capable of reducing an influx of calcium in the facial muscle and reduces the occurrence of an action potential in the facial muscle; and the *Acmella oleracea* extract is capable of reducing an influx of calcium in the facial muscle and reduces the occurrence of an action potential in the facial muscle. Embodiment 38 is the composition of any one of Embodiments 33 to 37, wherein the *Acmella oleracea* extract is capable of stimulating collagen production and laminin production in the skin. Embodiment 39 is the composition of any one of Embodiments 33 to 38, wherein the *Rosmarinus officinalis* leaf extract is capable of reducing matrix metalloproteinases 1, 3, or 9 production in the skin. Embodiment 40 is the composition of any one of Embodiments 33 to 39, wherein the composition is an emulsion, preferably an oil-in-water emulsion, or a gel.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations refer to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

The terms "wt. %," "vol. %," or "mol. %" refers to a weight, volume, or molar percentage of a component, respectively, based on the total weight, the total volume, or the total moles of material that includes the component. In a non-limiting example, 10 grams of component in 100 grams of the material is 10 wt. % of component. The term "% w/w" has the same meaning as wt. %.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is the ability to reduce the appearance of fine lines or wrinkles and/or reduce muscle contraction, preferably facial muscle contraction.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION OF ILLUSTRATIVE EMBODIMENTS

Figure 1:
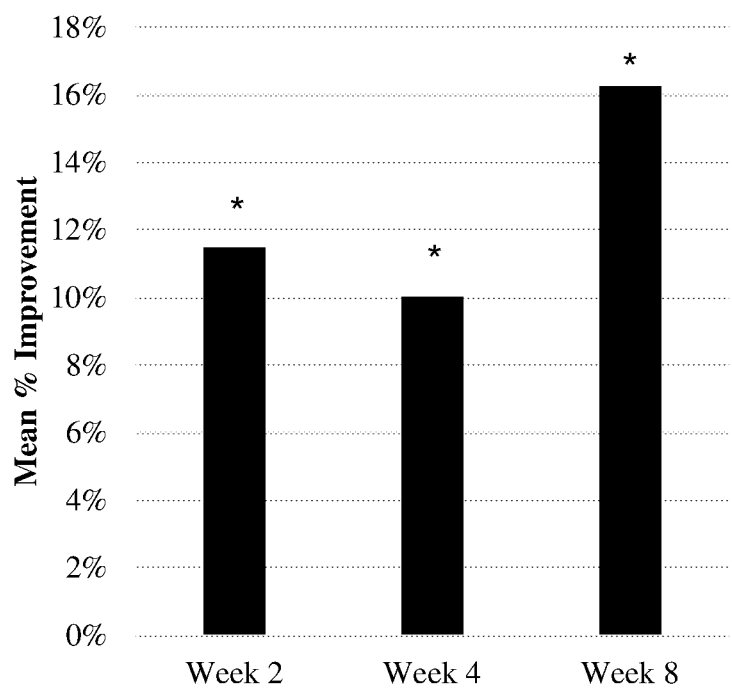
FIG. 1 provides data illustrating the mean % of improvement from baseline (0 week) in the EMG response area (mV.s) for muscle contraction in the glabella region for a group of people using a composition of the present invention having a combination of *Rosmarinus* officinalis leaf extract, *Lavendula* stoechas extract, and *Acmella* oleracea extract. The mean % of improvement illustrates reduced muscle contraction in the glabella region over time (2 weeks, 4 weeks, and 8 weeks). "*" indicates $p<0.05$ statistically significant improvement when compared to baseline (0 weeks).

A discovery has been made that provides a solution to at least some of the problems associated with current methods that are used to treat fine lines or wrinkles in skin, including both static and dynamic fine lines or wrinkles. Fine lines are typically characterized as smaller and shallower (e.g., generally less than two millimeters in depth) when compared to wrinkles, which have deeper lines (e.g., generally two or more millimeters in depth). Static fine lines or wrinkles are typically associated with fine lines or wrinkles that are present on skin that is relaxed/not-moving. By comparison, dynamic fine lines or wrinkles appear on skin with skin movement associated with muscle contraction. The solution is premised on using a combination of at least two of, and preferably, all three of, *Rosmarinus officinalis* leaf extract, *Lavendula stoechas* extract, and *Acmella oleracea* extract in topical skin compositions to reduce muscle contraction, preferably reduce muscle contraction in facial muscles. It is believed that the combination of these ingredients can help reduce the appearance of static and/or dynamic fine lines or wrinkles on at least three levels: (1) reducing muscle contraction in instances where muscle contraction can form the presence of fine lines or wrinkles (e.g., dynamic fine lines or wrinkles); (2) increasing collagen production in skin (e.g., in skin cells such as keratinocytes and/or fibroblasts), which can allow for more full and firm skin, which can lead to reduced appearance of static and/or dynamic fine lines or wrinkles; (3) decreasing matrix metalloproteinase (MMP) production or activity (the terms "production" and "activity" can be used interchangeably throughout this specification) in skin such as MMP-1, MMP-3, and/or MMP-9 production or activity to further help reduce the appearance of static and/or dynamic fine lines or wrinkles—MMP enzymes can breakdown or degrade extracellular matrix components such as collagen, fibronectin, laminin; proteoglycans, and vitronectin, which can lead to the formation of fine lines or wrinkles; and (4) increase laminin production in skin (e.g., skin cells such as keratinocytes and/or fibroblasts)—laminin is a structural glycoproteins located in the DEJ. Considered a glue that holds the cells together, laminin is secreted by dermal fibroblasts to help facilitate intra- and inter-cellular adhesion of the epidermal cells to the DEJ.

These and other non-limiting aspects of the present invention are described in the following sections.

A. Active Ingredients

The present invention is premised on a determination that a combination of active ingredients—*Rosmarinus officinalis* leaf extract, *Lavendula stoechas* extract, and/or *Acmella oleracea* extract—can be used to reduce muscle contraction of a facial muscle, reduce and/or prevent facial fine lines or wrinkles, reduce dynamic facial wrinkles and forehead wrinkles that are caused due to repetitive facial muscle contraction (e.g., rhytides), increase collagen production, reduce a matrix metalloproteinase, including one or more of matrix metalloproteinase 1, matrix metalloproteinase 3, and matrix metalloproteinase 9, firm skin, and/or reduce the appearance of loose, sagging, and flaccid skin.

*Rosmarinus officinalis* leaf extract is an extract from the leaf of *Rosmarinus officinalis*. *Rosmarinus officinalis* is native to the Mediterranean region, and is a woody, perennial herb with fragrant, evergreen, needle-like leaves and white, pink, purple, or blue flowers. It is a shrub that can reach up to 1.5 meters in height with leaves that are about 2 to 4 cm long with green (top surface) and white (bottom surface) coloring. In a preferred instance, the *Rosmarinus officinalis* leaf extract can be obtained from the leaf of *Rosmarinus officinalis*. The leaf can be subjected to a eutectigenesis extraction process using a fluid extraction mixture comprising betaine or hydrated betaine, a hydrogen bond donor compound (e.g., polyols, organic acids, etc.), and water. In particular, the leaf portion can be crushed or macerated and then subjected to the aforementioned eutectic fluid extraction mixture to obtain a eutectic extract. The eutectic extract can then be used in the compositions of the present invention. In some preferred instances, the hydrogen bond donor is an organic acid, preferably lactic acid. Eutectigenesis utilizes eutectic solvents which are mixtures of compounds having melting points lower than those of their constituents taken in isolation. In some instances, *Rosmarinus officinalis* is commercially available. In some instances, *Rosmarinus officinalis* can be supplied by Naturex (France) under the trade name ROSEMARY EUTECTYS BLA™. It was discovered in the context of the present invention that *Rosmarinus officinalis* leaf extract can reduce or inhibit contraction of myotubes by reducing or inhibiting an influx of calcium in the myotubes and reducing or preventing the occurrence of an action potential. It was also discovered that *Rosmarinus officinalis* leaf extract can inhibit or reduce MMP-1, MMP-3, and MMP-3 production or activity in skin cells (e.g., keratinocytes or human dermal fibroblasts).

*Lavendula stoechas* extract is an extract from the plant *Lavendula stoechas*. *Lavendula stoechas* is native to the Mediterranean region, and is an evergreen shrub that is about 30 to 100 cm tall with greyish and tomentose leaves that are about 1 to 4 cm long. In a preferred instance, the *Lavendula stoechas* extract is from a combination of the flower, leaf, and stem portions of *Lavendula stoechas*. These portions can be combined and then crushed or macerated or crushed or macerated and then combined. The resulting crushed or macerated flower/leaf/stem material can then subjected to a supercritical extraction process using carbon dioxide ($CO_2$) as the solvent. The supercritical $CO_2$ extract of *Lavendula stoechas* flower/leaf/stem can then be used in the compositions of the present invention. The $CO_2$ supercritical extract of the *Lavendula stoechas* flower/leaf/stem can also be mixed with caprylic/capric triglycerides and then used in the compositions of the present invention. In some instances, *Lavendula stoechas* extract is commercially available. In some instances, *Lavendula stoechas* can be supplied by Barnet Products LLC (Englewood Cliffs, N.J. (USA)) under the trade name STOCHEY'S. It was discovered in the context of the present invention that *Lavendula stoechas* extract can reduce or inhibit contraction of myotubes by reducing or inhibiting an influx of calcium in the myotubes and reducing or preventing the occurrence of an action potential.

*Acmella oleracea* extract is an extract from the *Acmella oleracea* plant. *Acmella oleracea* can be found in South America, Madagascar, and the Mascarene Islands. In a preferred instance, the *Acmella oleracea* extract is from the combination of the flower, leaf, and stem portions of *Acmella oleracea*. These portions can be combined and then crushed or macerated or crushed or macerated and then combined. The resulting crushed or macerated flower/leaf/stem material can then be subjected to a hydro-alcoholic (preferably hydro-ethanolic) extraction process or a hydro-alcoholic-polyol extraction process. The polyol in preferred instances can be 1,3-propanediol. The alcohol can be removed from the resulting extract. The *Acmella oleracea* extract can be then be used in the compositions of the present invention. In a preferred instance, the *Acmella oleracea* flower/leaf/stem extract can be obtained from a hydro-ethanol-1,3-propanediol solvent mixture. The resulting extract can then be used in the compositions of the present invention or can be further processed to remove the ethanol and can then be used in the compositions of the present invention. Alternatively, the extracting solvent can be a combination of water and polyol, preferably 1,3-propanediol, without an alcohol. The amounts of water, alcohol, and/or polyol present in the reaction mixture can be modified as desired. In some instances, *Acmella* oleracea extract is commercially available. In some instances, *Acmella oleracea* extract can be supplied by Gattefossé (France) under the trade name GATULINE® EXPRESSION AF. It was discovered in the context of the present invention that *Acmella oleracea* extract can reduce or inhibit contraction of myotubes by reducing or inhibiting an influx of calcium in the myotubes and reducing or preventing the occurrence of an action potential. It was also discovered that *Acmella oleracea* extract can increase both collagen production and laminin production in skin cells (e.g., keratinocytes or human dermal fibroblasts).

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc. In certain instances, each of the extracts can be prepared by: (i) obtaining the desired plant part (e.g., leaf, stem, bark, flower, seed, etc.) or whole plant; (ii) crushing or macerating the plant part or whole plant; (iii) optionally drying the crushed or macerated plant part or whole plant; (iv) subjecting the crushed or macerated plant or plant part to an extraction solvent to a sufficient period of time (e.g., 1, 5, 10, 30, or 45 minutes or more, or 1, 6, 12, or 18 hours or more, or 2, 3, 4, 5, 6 days, or more) under room temperature (e.g., 20 to 30° C.) or heated (e.g., greater than 30° C. or more, preferably 30° C. to less than the boiling point of the solvent); (v) collecting the solution comprising the extracting solvent and the extracted plant material (e.g., liquid extract); and (vi) optionally removing the extracting solvent to obtain a dried plant extract; and (vii) optionally reconstituting the dried plant extract in a liquid carrier (e.g., water, alcohol, diol, etc.). It is also contemplated in the context of the present invention that plant material from *Rosmarinus officinalis* leaf, *Lavendula stoechas*, and/or the *Acmella oleracea* can be directly used without subjecting the plant material to an extraction technique.

Non-limiting examples of facial muscles in which the compositions of the present invention can attenuate contraction of include facial muscles of the glabellar complex, orbicularis muscles, frontalis muscles, or depressor anguli oris muscles, or combinations thereof. The muscles of the glabellar complex can be responsible for formation of frown lines that include the corrugator supercilii, depressor supercilii, procerus, and orbicularis oculi para frontalis muscles. The corrugator supercilii lies below the frontalis muscle and functions to draw the brow medially and downward, whereas the smaller depressor supercilii can be located lower than the corrugator muscle and functions to draw the medial brow downward. The procerus can be located between the eyebrows and also works to depress the glabellar medial brow region. The depressor function of the glabellar complex is opposed by the frontalis muscle. This muscle is merged with the superior portions of the glabellar complex, from which it extends upwards underneath the forehead. The frontalis muscle is a muscle of the forehead and is associated with raising of the brow. The orbicularis muscle is a muscle that closes the eyelids. The depressor anguli oris muscle is a facial muscle associated with frowning. In a preferred aspect, contractile activity is measured.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of any ingredient within the compositions can vary. In non-limiting embodiments, for example, the compositions can comprise, consist essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., Stevia rebaudiana (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., Aloe vera, chamomile, cucumber extract, Ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, threonine, lysine, alanine, algae extract, Aloe barbadensis, Aloe barbadensis extract, Aloe barbadensis gel, Althea officinalis extract, apricot (Prunus armeniaca) kernel oil, arginine, arginine aspartate, Arnica montana extract, aspartic acid, avocado (Persea gratissima) oil, barrier sphingolipids, butyl alcohol, beeswax, behenyl alcohol, beta-sitosterol, birch (Betula alba) bark extract, borage (Borago officinalis) extract, butcherbroom (Ruscus aculeatus) extract, butylene glycol, Calendula officinalis extract, Calendula officinalis oil, candelilla (Euphorbia cerifera) wax, canola oil, caprylic/capric triglyceride, cardamom (Elettaria cardamomum) oil, carnauba (Copernicia cerifera) wax, carrot (Daucus carota sativa) oil, castor (Ricinus communis) oil, ceramides, ceresin, ceteareth-5, ceteareth-12, ceteareth-20, cetearyl ethylhexanoate, ceteth-20, ceteth-24, cetyl acetate, cetyl octanoate, cetyl palmitate, chamomile (Anthemis nobilis) oil, cholesterol, cholesterol esters, cholesteryl hydroxystearate, citric acid, clary (Salvia sclarea) oil, cocoa (Theobroma cacao) butter, coco-caprylate/caprate, coconut (Cocos nucifera) oil, collagen, collagen amino acids, corn (Zea mays) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, Eucalyptus globulus oil, evening primrose (Oenothera biennis) oil, fatty acids, Geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (Vitis vinifera) seed oil, hazel (Corylus americana) nut oil, hazel (Corylus avellana) nut oil, hexylene glycol, hyaluronic acid, hybrid safflower (Carthamus tinctorius) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, proline, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (Jasminum officinale) oil, jojoba (Buxus chinensis) oil, kelp, kukui (Aleurites moluccana) nut oil, lactamide MEA, laneth-16, laneth-10 acetate, lanolin, lanolin acid, lanolin alcohol, lanolin oil, lanolin wax, lavender (Lavandula angustifolia) oil, lecithin, lemon (Citrus medica limonum) oil, linoleic acid, linolenic acid, Macadamia ternifolia nut oil, maltitol, matricaria (Chamomilla recutita) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (Olea europaea) oil, orange (Citrus aurantium dulcis) oil, palm (Elaeis guineensis) oil, palmitic acid, pantethine, panthenol, panthenyl ethyl ether, paraffin, PCA, peach (Prunus persica) kernel oil, peanut (Arachis hypogaea) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (Mentha piperita) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (Oryza sativa) bran oil, RNA, rosemary (Rosmarinus officinalis) oil, rose oil, safflower (Carthamus tinctorius) oil, sage (Salvia officinalis) oil, sandalwood (Santalum album) oil, serine, serum protein, sesame (Sesamum indicum) oil, shea butter (Butyrospermum parkii), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (Glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (Helianthus annuus) seed oil, sweet almond (Prunus amygdalus dulcis) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (Triticum vulgare) germ oil, and ylang (Cananga odorata) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCL, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, hydroxypropyl cyclodextrin, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds include silicone oils such as a polyorganosiloxane. Non-limiting examples of polyorganosiloxanes include dimethicone, cyclomethicone, cyclohexasiloxane, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyl-taurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid cross-linked with allyl ethers of sucrose or pentaerythritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

In Vitro Myotube Contraction Data

Each of *Rosmarinus* officinalis leaf extract, *Lavendula* stoechas extract, and *Acmella* oleracea extract were found to reduce contraction of myotubes, which can result in reduced muscle contraction of a facial muscle and reduced appearance of facial deep lines or wrinkles and dynamic facial wrinkles and forehead wrinkles that are caused due to repetitive facial muscle contraction. The methodology used to obtain the data included: (1) Primary Human Skeletal muscle myoblasts (HSMM) were made to differentiate into Myotubes; (2) Myotubes were then treated with 'inducers' (Acetcholine), which in turn causes an influx of calcium and creating an action potential; and (3) This action potential causes the muscle cells to contract. The concentration amounts of each extract used and the resulting effect on inhibition of calcium levels are provided in Table 1.

TABLE 1

| Ingredient | Inhibition of Calcium Levels |
| --- | --- |
| *Rosmarinus Officinalis* Leaf extract* | 1.0 wt. % conc. = 100% inhibition |
|  | 2.0 wt. % conc. = 100% inhibition |
| *Lavendula Stoechas* Extract** | 0.5% wt. conc. = 30% inhibition |
|  | 1.0% wt. conc. = 30% inhibition |
| *Acmella Oleracea* Extract*** | 0.5% wt. conc. = 77% inhibition |
|  | 1.0% wt. conc. = 96% inhibition |

*Rosmarinus officinalis* leaf extract was a eutectic extract in which the solvent used to prepare the extract was a fluid mixture of betaine, lactic acid, and water. The extract was supplied by Naturex (France) under the trade name ROSEMARY EUTECTYS BLA ™.
**Lavendula stoechas* extract used was a supercritical $CO_2$ extract of the flower/leaf/stem of *Lavendula stoechas*. The $CO_2$ extract was mixed with caprylic/capric triglycerides. The extract was supplied by Barnet Products LLC (Englewood Cliffs, New Jersey (USA)) under the trade name STOCHEY'S.
***Acmella oleracea* extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name GATULINE ® EXPRESSION AF.

Example 2

In Vitro Collagen Expression Data

*Acmella oleracea* extract was found to increase collagen production in human dermal fibroblasts. The data and amount of extract used is provided in Table 2.

TABLE 2

| Ingredient | Increased Collagen Production |
| --- | --- |
| *Acmella Oleracea* Extract* | 1.0 wt. % conc. = 61% increased collagen production |

*Acmella oleracea* extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name GATULINE ® EXPRESSION AF.

Collagen is an extracellular matrix protein critical for skin structure. Increased synthesis of collagen helps improve skin firmness and elasticity. This bioassay was used to examine the effect of *Acmella oleracea* extract on the production of procollagen peptide (a precursor to collagen) by human dermal fibroblasts. The endpoint of this assay was a spectrophotometric measurement that reflected the presence of procollagen peptide and cellular viability. The assay employed the quantitative sandwich enzyme immunoassay technique whereby a monoclonal antibody specific for procollagen peptide was pre-coated onto a microplate. Standards and samples were pipetted into the wells and any procollagen peptide present was bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells and color developed in proportion to the amount of procollagen peptide bound in the initial step. Color development was stopped and the intensity of the color at 450 nm was measured using a microplate reader.

For generation of samples and controls, subconfluent normal human adult dermal fibroblasts (Cascade Biologics) were cultivated in standard DMEM growth medium with 10% fetal bovine serum (Mediatech) at 37° C. in 10% $CO_2$. The cells were treated with each of the tested ingredients and controls for 3 days. Following incubation, cell culture medium was collected and the amount of procollagen peptide secretion was quantified using the sandwich enzyme linked immuno-sorbant assay (ELISA) from Takara (#MK101) as explained above.

Example 3

In Vitro Laminin Expression Data

*Acmella* oleracea extract was found to increase laminin production in human dermal fibroblasts. The data and amount of extract used is provided in Table 3.

TABLE 3

| Ingredient | Increased Laminin Production |
| --- | --- |
| *Acmella Oleracea* Extract* | 1.0 wt. % conc. = 53% increased laminin production |

*Acmella oleracea* extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name GATULINE ® EXPRESSION AF.

Laminin is a major protein in the dermal-epidermal junction (DEJ) (also referred to as the basement membrane). The DEJ is located between the dermis and the epidermis and interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin is a structural glycoproteins located in the DEJ. Considered a glue that holds the cells together, laminin is secreted by dermal fibroblasts to help facilitate intra- and inter-cellular adhesion of the epidermal cells to the DEJ. Laminin secretion was monitored by quantifying laminin in cell supernatants of cultured human fibroblasts treated for 3 days with culture medium with the test ingredient (*Acmella oleracea* extract). Following incubation, laminin was measured using immunofluorescent antibodies directed against each protein in an enzyme linked immuno-sorbant assay (ELISA). Measurements were normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Example 4

In Vitro MMP Inhibition Data

*Rosmarinus officinalis* leaf extract was found to inhibit matrix metalloproteinases (MMP) 1, 3, and 9 in human dermal fibroblasts. The data and amount of extract used is provided in Table 4.

TABLE 4

| Ingredient | Inhibition of MMP-1, 3, and 9 Production |
| --- | --- |
| *Rosmarinus Officinalis* Leaf extract* | MMP-1 @ 1.0 wt. % conc. = −98% inhibition |
|  | MMP-3 @ 1.0 wt. % conc. = −39% inhibition |
|  | MMP-9 @ 1.0 wt. % conc. = −61% inhibition |

*Rosmarinus officinalis* leaf extract was a eutectic extract in which the solvent used to prepare the extract was a fluid mixture of betaine, lactic acid, and water. The extract was supplied by Naturex (France) under the trade name ROSEMARY EUTECTYS BLA ™.

Matrix Metalloproteinase 1 Enzyme Activity (MMP-1) Assay: MMPs are extracellular proteases that play a role in many normal and disease states by virtue of their broad substrate specificity. MMP-1 substrates include collagen IV. The Molecular Probes Enz/Chek Gelatinase/ Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity. The Enz/Chek Gelatinase/Collagenase Assay kit (#E12055) from Invitrogen is designed as an in vitro assay to measure MMP-1 enzymatic activity. The *Rosmarinus officinalis* leaf extract was assayed. The assay relies upon the ability of purified MMP-1 enzyme to degrade a fluorogenic gelatin substrate. Once the substrate is specifically cleaved by MMP-1 bright green fluorescence is revealed and was monitored using a fluorescent microplate reader. *Rosmarinus officinalis* leaf extract was incubated in the presence or absence of the purified enzyme and substrate to determine their protease inhibitor capacity.

Matrix Metalloproteinase 3 and 9 Enzyme Activity (MMP-3 and MMP-9) Assay: MMP-3 substrates include collagens, fibronectins, and laminin; while MMP-9 substrates include collagen VII, fibronectins and laminin. Using Colorimetric Drug Discovery kits from BioMol International for MMP3 (AK-400) and MMP-9 (AK-410), this assay was designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2- nitrobenzoic acid), Ellman's reagent] to form 2-nitro-5-thiobenzoic acid, which can be detected by its absorbance at 412 nm ($\varepsilon$=13,600 M-1 cm-1 at pH 6.0 and above 7). The *Rosmarinus* officinalis leaf extract was assayed.

Example 5

In Vivo Clinical Data

In vivo clinical data on the combination of *Rosmarinus officinalis* leaf extract, *Lavendula stoechas* extract, and *Acmella oleracea* extract was obtained. The *Rosmarinus officinalis* leaf extract was a eutectic extract in which the solvent used to prepare the extract was a fluid mixture of betaine, lactic acid, and water. The extract was supplied by Naturex (France) under the trade name ROSEMARY EUTECTYS BLA™. The *Lavendula stoechas* extract used was a supercritical $CO_2$ extract of the flower/leaf/stem of *Lavendula* stoechas. The $CO_2$ extract was mixed with caprylic/capric triglycerides. The extract was supplied by Barnet Products LLC (Englewood Cliffs, N.J. (USA)) under the trade name STOCHEY'S. The *Acmella* oleracea extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name GATULINE® EXPRESSION AF.

The purpose of the in vivo clinical study was to evaluate the efficacy of a combination of the three extracts for muscle relaxation and wrinkle reduction over four weeks of twice-daily application on 30 individuals (n=30). The combination of the three extracts was placed in a dermatologically acceptable vehicle. The dermatologically acceptable vehicle was designed to test the efficacy of the combination of the three extracts. The other ingredients in the dermatologically acceptable vehicle were not believed to contribute to the clinical data results in either a positive or negative manner. The amounts of each extract used in the dermatologically acceptable vehicle was *Rosmarinus officinalis* leaf extract at 1 wt. %, *Lavendula stoechas* extract at 2 wt. %, and *Acmella oleracea* extract at 2 wt. %.

The in vivo clinical study design was a randomized controlled, investigator-blinded clinical study. The following parameters were used: (1) subjects—females between the ages of 35 and 70 in good general health (no physical required) and were clinically determined to have scored 3-7 (inclusively) on a 10-point scale for moderate frown/glabellar lines; (2) test site—glabella area; (3) evaluation time points—baseline (week 0), week 2, week 4, and week 8; (4) testing method—electromyography (EMG) for muscle response (mV/s):AUC (area under the curve); and (5) clinical endpoints measured—fine lines and wrinkles and skin texture on a 0 to 9 scale.

Figure 2:
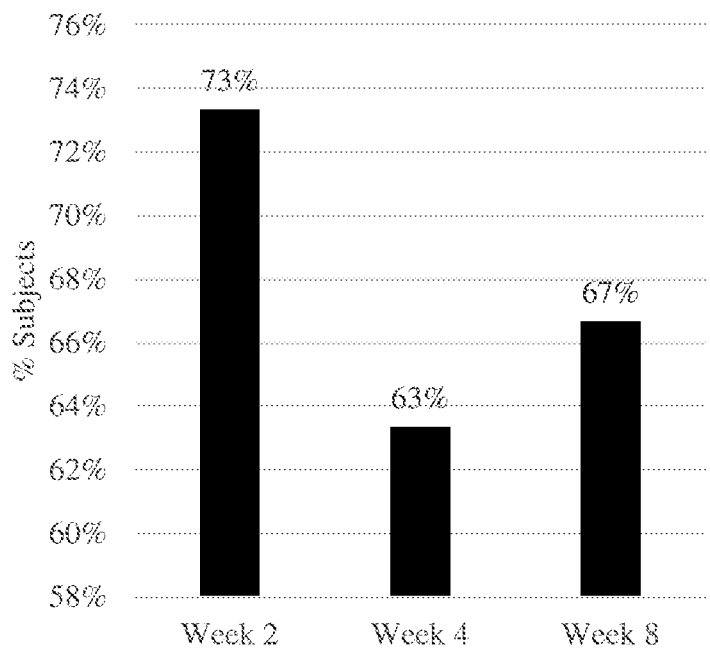
FIG. 2 provides data illustrating the % of people showing improvement from baseline (0 week) in the EMG response area (mV.s) for muscle contraction in the glabella region for a group of people using a composition of the present invention having a combination of *Rosmarinus* officinalis leaf extract, *Lavendula stoechas* extract, and *Acmella oleracea* extract. The % of people showing improvement illustrates reduced muscle contraction in the glabella region over time (2 weeks, 4 weeks, and 8 weeks).
Figure 3:
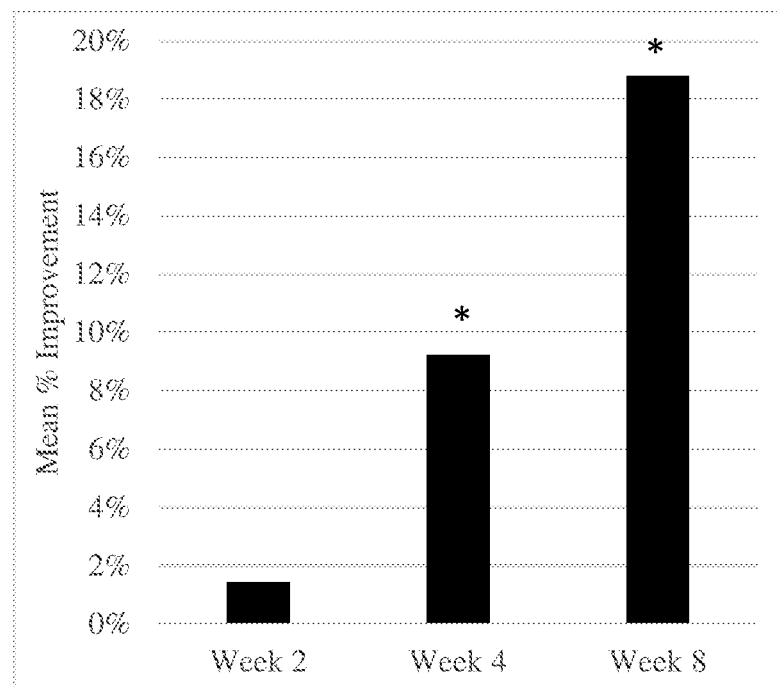
FIG. 3 provides data illustrating the mean % of improvement from baseline (0 week) for reduced appearance of fine lines and wrinkles for a group of people using a composition of the present invention having a combination of *Rosmarinus officinalis* leaf extract, *Lavendula stoechas* extract, and *Acmella oleracea* extract. The mean % of improvement illustrates reduced appearance of fine lines and wrinkles in the treated area over time (2 weeks, 4 weeks, and 8 weeks). "*" indicates p<0.05 statistically significant improvement when compared to baseline (0 weeks).
Figure 4:
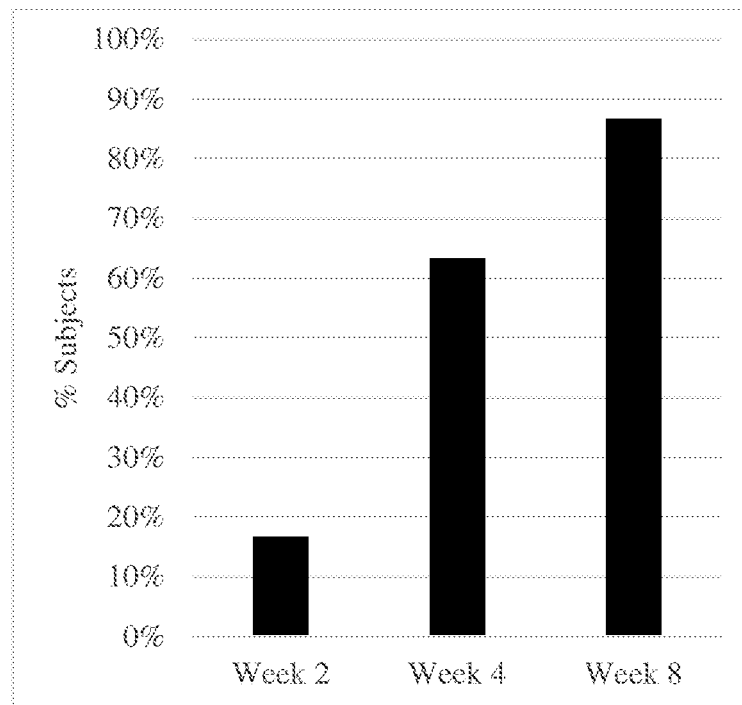
FIG. 4 provides data illustrating the % of people showing improvement from baseline (0 week) in the reduction of fine lines and wrinkles for a group of people using a composition of the present invention having a combination of *Rosmarinus officinalis* leaf extract, *Lavendula stoechas* extract, and *Acmella oleracea* extract. The % of people showing improvement illustrates reduced appearance of fine lines and wrinkles in the treated area over time (2 weeks, 4 weeks, and 8 weeks).

FIGS. 1-2 provide data illustrating muscle contraction inhibition via EMG testing. FIGS. 3-4 provide data illustrating reduction in the appearance of fine lines and wrinkles. As illustrated in these FIGS. 1-4, the data suggests that the combination of *Rosmarinus officinalis* leaf extract, *Lavendula stoechas* extract, and *Acmella oleracea* extract can reduce facial muscle contraction and can reduce the overall appearance of fine lines and wrinkles. The following Table 5 provides data illustrating the EMG response and clinical comparison between a well-known injectable neuromodulator (Botox® (onabotulinumtoxinA)) and the combination of *Rosmarinus* officinalis leaf extract, *Lavendula* stoechas extract, and *Acmella oleracea* extract.

TABLE 5

| | % EMG Response (AUC) | | % Clinical Improvement of Wrinkles | |
|---|---|---|---|---|
| | BoTox - 5 U (n = 5)** | Combination of three extracts (n = 30) | BoTox - 5 U (n = 5)** | Combination of three extracts (n = 30) |
| Week 2 | 58%* | 11% | 31%* | 1% |
| Week 4 | 40%* | 10% | 35%* | 9%* |
| Week 8 | Not measured | 16%* | Not measured | 19%* |

*$p < 0.05$ statistically significant improvement when compared to baseline.
**The BoTox - 5 U study was used as a control to validate the method and performed on 5 individuals. Each individual was administered 5 units (U) of Botox to the glabella region and % EMG Response (AUC) was measured. This was done to standardize the aforementioned combination of extracts study.

Example 6

In Vivo Clinical Data

In a comparative clinical study, additional in vivo clinical data on the combination of *Rosmarinus officinalis* leaf extract, *Lavendula stoechas* extract, and *Acmella oleracea* extract was obtained. The *Rosmarinus officinalis* leaf extract was a eutectic extract in which the solvent used to prepare the extract was a fluid mixture of betaine, lactic acid, and water. The extract was supplied by Naturex (France) under the trade name ROSEMARY EUTECTYS BLA™. The *Lavendula stoechas* extract used was a supercritical $CO_2$ extract of the flower/leaf/stem of *Lavendula stoechas*. The $CO_2$ extract was mixed with caprylic/capric triglycerides. The extract was supplied by Barnet Products LLC (Englewood Cliffs, N.J. (USA)) under the trade name STOCHEY'S. The *Acmella oleracea* extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name GATULINE® EXPRESSION AF.

The purpose of the comparative in vivo clinical study was to evaluate the efficacy of a combination of the three extracts for muscle relaxation and wrinkle reduction over four weeks of twice-daily application on Experimental Group 1 participants using a micro-roller (n=33) versus application on Experimental Group 2 participants without using a micro-roller (n=30). The combination of the three extracts was placed in a dermatologically acceptable vehicle as the test product. The dermatologically acceptable vehicle was designed to test the efficacy of the combination of the three extracts when applied with a micro-roller versus application without a micro-roller. Study participants in Experimental Group 1 used a 1.0 mm microroller. Study participants applied the composition containing the three extracts between their eyebrows in the morning and the evening after cleansing their face with a personal cleanser. For Experimental Group 1, study participants used the micro-roller 3 times per week in the evenings by rolling the micro-roller back and forth 4 to 5 times between eyebrows changing directions with each pass. For both Experimental Group 1 and Experimental Group 2, an occlusive patch (e.g., SCARAWAY®) was placed between eyebrows overnight. The other ingredients in the dermatologically acceptable vehicle were not believed to contribute to the clinical data results in either a positive or negative manner. The amounts of each extract used in the dermatologically acceptable vehicle was *Rosmarinus* officinalis leaf extract at 1 wt. %, *Lavendula stoechas* extract at 2 wt. %, and *Acmella oleracea* extract at 2 wt. %.

The comparative in vivo clinical study design was a randomized controlled, investigator-blinded clinical study. The following parameters were used: (1) subjects—females between the ages of 35 and 70 in good general health (no physical required) and were clinically determined to have scored 3-7 (inclusively) on a 10-point scale for moderate frown/glabellar lines; (2) test site—glabella area; (3) test product—Frontalis; supplemental products—SCARAWAY® occlusive patch, and microroller; (4) evaluation time points—baseline (week 0), week 2, week 4, and week 8; (5) testing method—electromyography (EMG) for muscle response (mV/s):AUC (area under the curve); and (6) clinical endpoints measured—fine lines and wrinkles and skin texture on a 0 to 9 scale.

Figure 5:
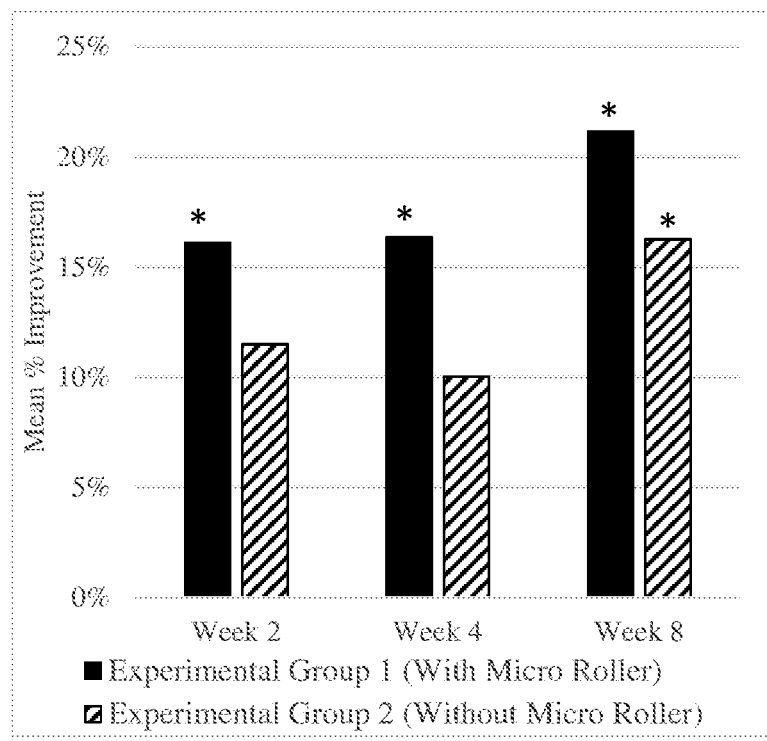
FIG. 5 provides data illustrating the mean % of improvement from baseline (0 week) in the EMG response area (mV.s) for muscle contraction in the glabella region for a group of people using a composition of the present invention having a combination of *Rosmarinus officinalis* leaf extract, *Lavendula stoechas* extract, and *Acmella oleracea* extract, and applying the composition with a micro-roller versus applying the composition without a micro-roller. The mean % of improvement illustrates a faster and stronger reduction in facial muscle contraction at 2, 4, and 8 weeks compared to baseline when using a micro-roller with application of the composition. "*" indicates p<0.05 statistically significant improvement when compared to baseline (0 weeks).
Figure 6:
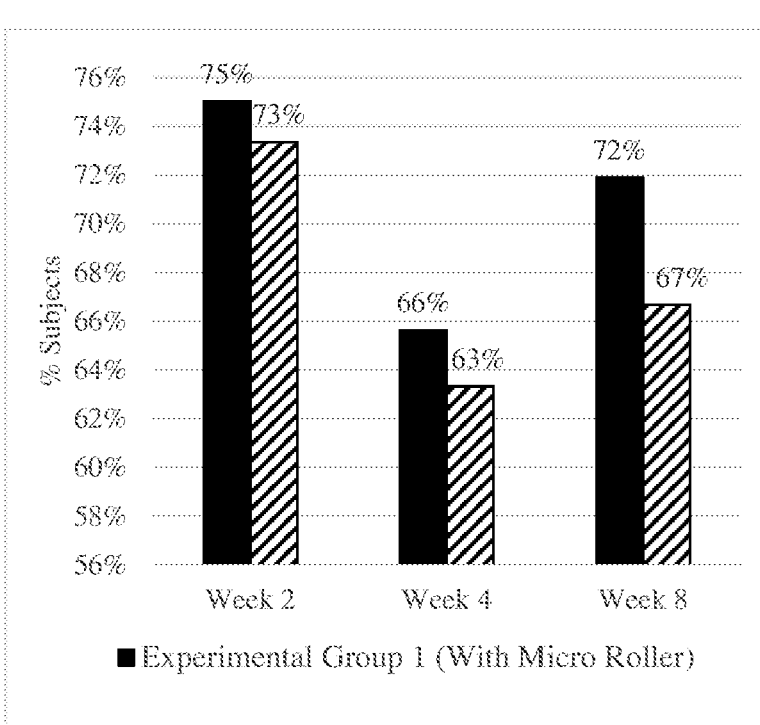
FIG. 6 provides data illustrating the % of people showing improvement from baseline (0 week) in the EMG response area (mV.s) for muscle contraction in the glabella region for a group of people using a composition of the present invention having a combination of *Rosmarinus officinalis* leaf extract, *Lavendula stoechas* extract, and *Acmella oleracea* extract. The % of people showing improvement illustrates a faster and stronger reduction in facial muscle contraction at 2, 4, and 8 weeks in the glabella region when using a micro-roller with application of the composition.
Figure 7:
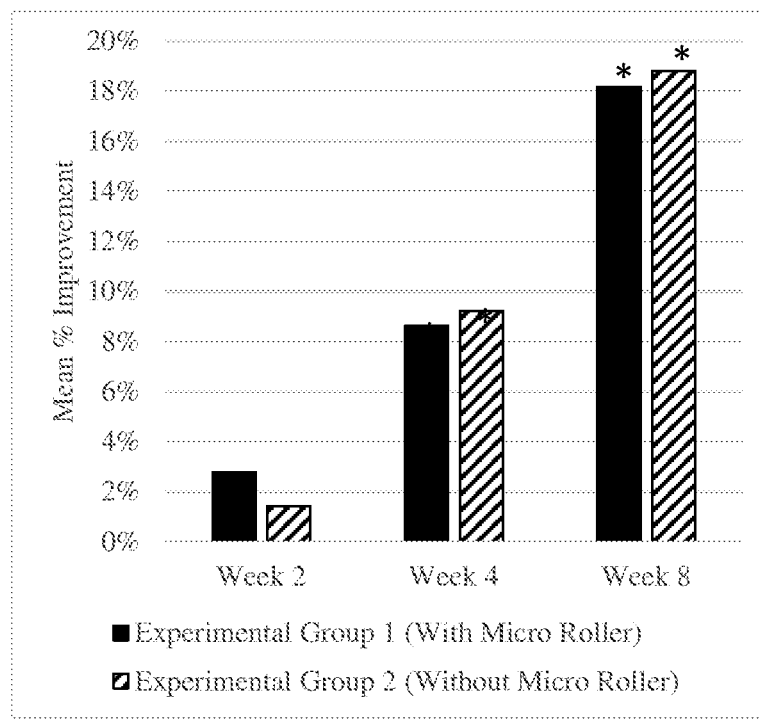
FIG. 7 provides data illustrating the mean % of improvement from baseline (0 week) for reduced appearance of fine lines and wrinkles for a group of people using a composition of the present invention having a combination of *Rosmarinus officinalis* leaf extract, *Lavendula stoechas* extract, and *Acmella oleracea* extract. The mean % of improvement illustrates reduced appearance of fine lines and wrinkles in the treated area over time (2 weeks, 4 weeks, and 8 weeks) when using a micro-roller with application of the composition and without using a micro-roller with application of the composition. "*" indicates p<0.05 statistically significant improvement when compared to baseline (0 weeks).
Figure 8:
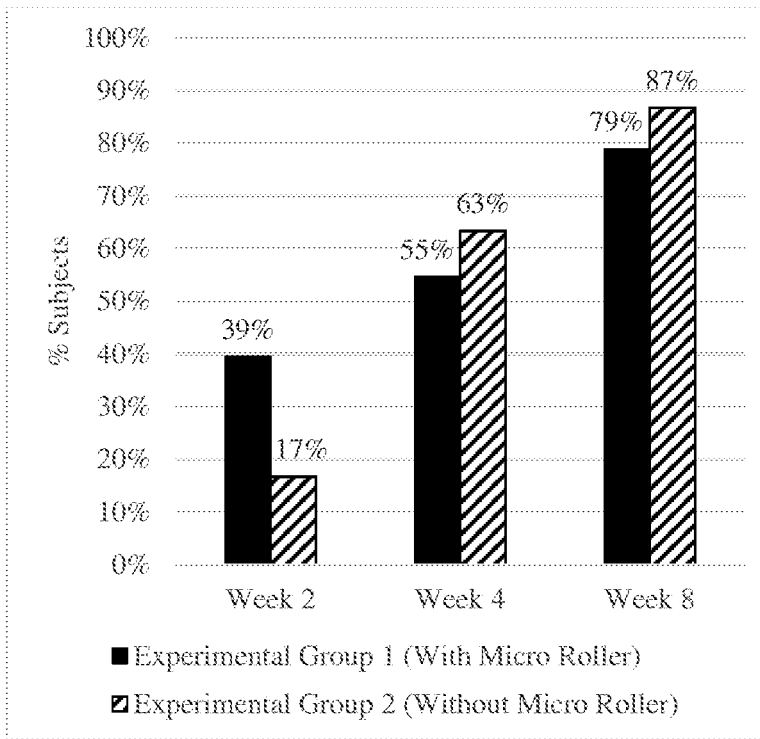
FIG. 8 provides data illustrating the % of people showing improvement from baseline (0 week) in the reduction of fine lines and wrinkles for a group of people using a composition of the present invention having a combination of *Rosmarinus officinalis* leaf extract, *Lavendula stoechas* extract, and *Acmella oleracea* extract. The % of people showing improvement illustrates reduced appearance of fine lines and wrinkles in the treated area over time (2 weeks, 4 weeks, and 8 weeks) when using a micro-roller with application of the composition and without using a micro-roller with application of the composition.

FIGS. 5-6 provide data illustrating muscle contraction inhibition via EMG testing comparing percent improvement between application with a micro-roller and application without a micro-roller. FIGS. 7-8 provide data illustrating reduction in the appearance of fine lines and wrinkles comparing percent improvement between application with a micro-roller and application without a micro-roller. As illustrated in FIGS. 5-8, the data suggests that application of the composition containing the combination of *Rosmarinus officinalis* leaf extract, *Lavendula stoechas* extract, and *Acmella oleracea* extract, combined with using a micro-roller to promote penetration of the composition into the skin, can reduce facial muscle contraction and can reduce the overall appearance of fine lines and wrinkles. It was determined that application of the composition with a micro-roller was effective at attaining a faster and stronger reduction in facial muscle contraction at 2, 4, and 8 weeks compared to baseline, and reduced fine lines and wrinkles and skin texture within 4 weeks, where 79% of subjects showed improvement in both fine lines and wrinkles and skin smoothness after 8 weeks. It was further determined that application of the composition without a micro-roller was still effective at attaining a reduction in facial muscle contraction after 8 weeks, and reduced fine lines and wrinkles and skin texture within 4 weeks, where 87% of subjects showed improvement in both fine lines and wrinkles and 90% in skin smoothness after 8 weeks.

Figure 9:
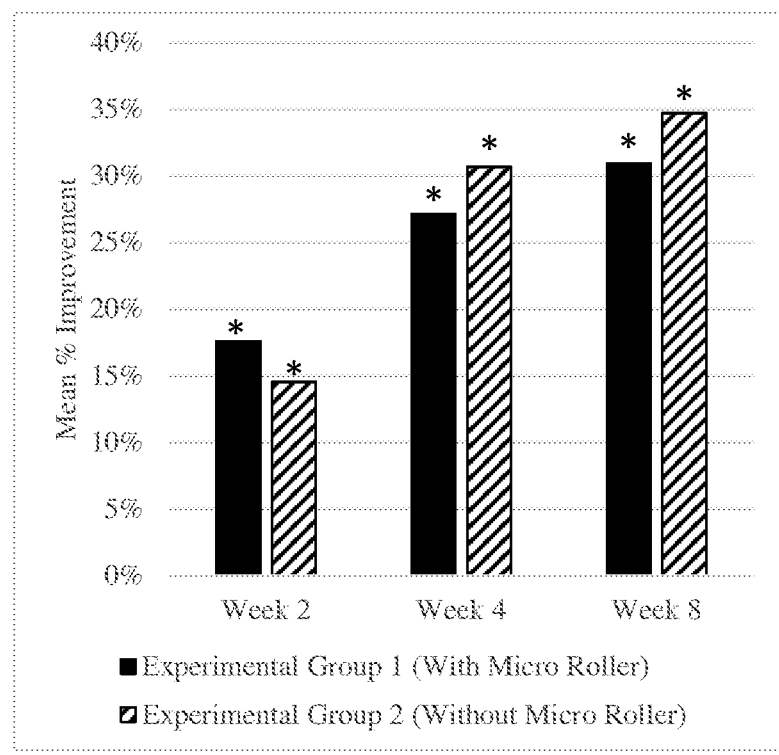
FIG. 9 provides data illustrating the mean % of improvement from baseline (0 week) for skin texture/roughness for a group of people using a composition of the present invention having a combination of *Rosmarinus officinalis* leaf extract, *Lavendula stoechas* extract, and *Acmella oleracea* extract. The mean % of improvement illustrates improved skin texture/roughness in the treated area over time (2 weeks, 4 weeks, and 8 weeks) when using a micro-roller with application of the composition and without using a micro-roller with application of the composition. "*" indicates p<0.05 statistically significant improvement when compared to baseline (0 weeks).
Figure 10:
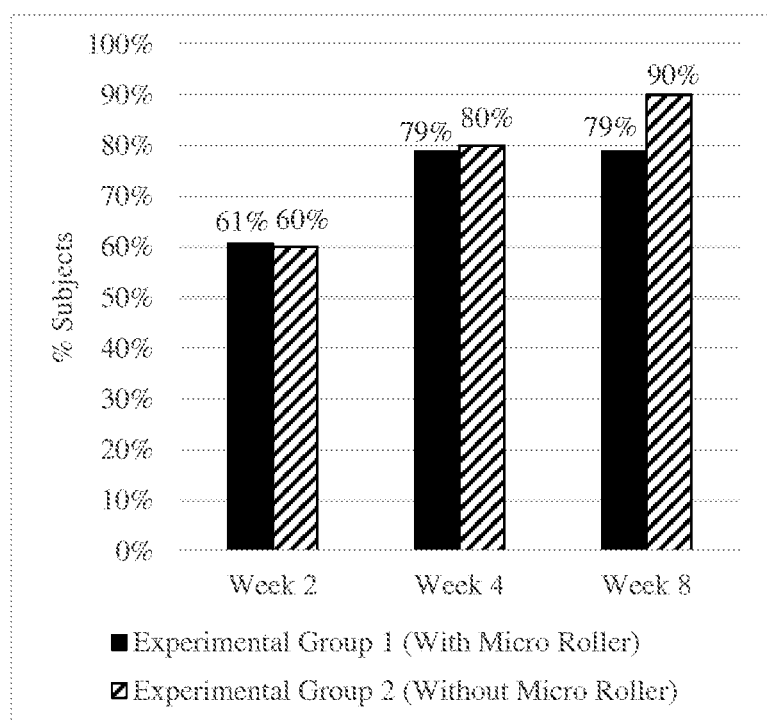
FIG. 10 provides data illustrating the % of people showing improvement from baseline (0 week) in skin texture/roughness for a group of people using a composition of the present invention having a combination of *Rosmarinus officinalis* leaf extract, *Lavendula stoechas* extract, and *Acmella oleracea* extract. The % of people showing improvement illustrates improved skin texture/roughness in the treated area over time (2 weeks, 4 weeks, and 8 weeks) when using a micro-roller with application of the composition and without using a micro-roller with application of the composition.

FIGS. 9-10 provide data illustrating improvement in skin texture/roughness comparing percent improvement between application with a micro-roller and application without a micro-roller. As illustrated in FIGS. 9-10, the data suggests that application of the composition containing the combination of *Rosmarinus officinalis* leaf extract, *Lavendula stoechas* extract, and *Acmella oleracea* extract, combined with using a micro-roller to promote penetration of the composition into the skin, can significantly improve skin texture and roughness in the glabellar area after 2, 4, and 8 weeks. It was determined that 79% of subjects showed improvement in skin smoothness after 8 weeks after application of the composition with a micro-roller. It was further determined that application of the composition without a micro-roller was still effective at improving skin smoothness after 8 weeks.

The following Table 6 provides data illustrating the EMG response and clinical comparison between a well-known injectable neuromodulator (Botox® (onabotulinumtoxinA)) and the combination of *Rosmarinus officinalis* leaf extract, *Lavendula stoechas* extract, and *Acmella oleracea* extract applied with a micro-roller and applied without a micro-roller.

TABLE 6

|  | % EMG Response (AUC) | | | % Clinical Improvement of Wrinkles | | |
| --- | --- | --- | --- | --- | --- | --- |
|  | BoTox - 5U (n = 5)** | Experimental Group 1 (w/micro-roller) (n = 33) | Experimental Group 2 (w/o micro-roller) (n = 30) | BoTox - 5U (n = 5)** | Experimental Group 1 (w/micro-roller) (n = 33) | Experimental Group 2 (w/o micro-roller) (n = 30) |
| Week 2 | 58%* | 16%* | 11% | 31%* | 3% | 1% |
| Week 4 | 40%* | 16%* | 10% | 35%* | 9%* | 9%* |
| Week 8 | Not measured | 21%* | 16%* | Not measured | 18%* | 19%* |

*p < 0.05 statistically significant improvement when compared to baseline.

**The BoTox - 5U study was used as a positive control in comparing Experimental Group 1 and Experimental Group 2 and was performed on 5 individuals. Each individual was administered 5 units (U) of Botox to the glabella region and % EMG Response (AUC) was measured. This was done to standardize the aforementioned combination of extracts study.

Example 7

Additional Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Antioxidant (AO) Assay: An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®·+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations.

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (#AOX-2)). The Zen-Bio ORAC Antioxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygenase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachidonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion is measured by absorbance at 405 nm and cellular viability was quantified.

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers can be monitored in cultured human fibroblasts by staining of cultured human fibroblasts using immunofluorescent antibodies directed against elastin.

Laminin and Fibronectin Stimulation Assay: Laminin and fibronectin are major proteins in the dermal-epidermal junction (DEJ) (also referred to as the basement membrane). The DEJ is located between the dermis and the epidermis and interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal cells to the DEJ. Laminin and fibronectin secretion can be monitored by quantifying laminin and fibronectin in cell supernatants of cultured human fibroblasts treated for 3 days with culture medium with or without the test ingredient(s). Following incubation, laminin and fibronectin content can be measured using immunofluorescent antibodies directed against each protein in an enzyme linked immuno-sorbant assay (ELISA). Measurements are normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color developed in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EPILIFE™ standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition can be compared with that of kojic acid (Sigma).

Elastase Assay: ENZCHEK® Elastase Assay (Kit #E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin.

This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin: Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMON™ western blotting protocol. For each sample, normal human epidermal keratinocytes (NHEK) are grown in EPI-200-Mattek EPILIFE™ growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin: Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% CO2 for 24 hours in EPILIFE™ growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in EPILIFE™ growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample—Percent Permeability of untreated control.

Production of Hyaluronic Acid: Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay. Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm—inhibitor reaction wells absorbance at 600 nm); Initial activity=control enzyme absorbance at 600 nm; Percent Inhibition=[(Initial activity/Inhibitor Activity)*100]-100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine array: Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180× g to form a pellet of cells. The supernatant is aspirated. The resulting pellet is resuspended in EPILIFE™ media (Cascade Biologics). The cells are seeded in 6-well plates at approximately 10-20% confluency. After the cells became approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 µl of 100× stock) and 0.1% (10 µl of 100× stock) test compositions are diluted into a final volume of 1 ml EPILIFE™ Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FASTFrame (4 slides per frame) for processing. Arrays are blocked for 15 min. at room temp. using 70 ml S&S Protein Array Blocking buffer (Whatman Schleicher and Scheull). Blocking buffer is removed and 70 ml of each supernatant sample is added to each array. Arrays are incubated for 3 hours at room temp. with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temp. with gentle agitation. Arrays are washed 3 times with TBS-T. Arrays are incubated with 70 ml of a solution containing streptavidin-Cy5 conjugate for 1 hour at room temp. with gentle agitation. Arrays are washed 3 times with TBS-T, quickly rinsed in deionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 µg/ml bovine brain extract, 1 µg/ml hydrocortisone, and 1 µg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 µl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method for reducing muscle contraction of a facial muscle in a person and reducing the appearance of a rhytide on a person's facial skin caused by the facial muscle, the method comprising topically applying to skin within 3 cm of the facial muscle causing the rhytide a composition comprising:
   (a) an effective amount of *Rosmarinus officinalis* leaf extract;
   (b) an effective amount of *Lavendula stoechas* extract;
   (c) alcohol;
   (d) pentylene glycol;
   (e) stearyl alcohol;
   (f) caprylic/capric triglycerides;
   (g) ethoxydiglycol;
   (h) propylene glycol; and
   (i) triethanolamine,
wherein topical application of the composition to the rhytide reduces muscle contraction of the facial muscle and reduces the appearance of the rhytide;
wherein the *Rosmarinus officinalis* leaf extract is obtained with a fluid extraction solvent mixture comprising betaine, lactic acid, and water; and
wherein the *Lavendula stoechas* extract is a *Lavendula stoechas* flower/leaf/stem extract obtained with a supercritical carbon dioxide ($CO_2$) extraction solvent.

2. The method of claim 1, wherein the *Rosmarinus officinalis* leaf extract and the *Lavendula stoechas* extract reduce an influx of calcium in the facial muscle and reduce the occurrence of an action potential in the facial muscle.

3. The method of claim 1, wherein the facial muscle is a glabellar complex muscle, an orbicularis oculi muscle, a depressor muscle, or a frontalis muscle, or any combination thereof.

4. The method of claim 1, wherein the *Rosmarinus officinalis* leaf extract reduces matrix metalloproteinases 1, 3, or 9 production in the skin.

5. The method of claim 1, wherein the composition comprises:
  0.00001 to 10% w/w of *Rosmarinus officinalis* leaf extract; and
  0.00001 to 10% w/w of *Lavendula stoechas* extract.

6. The method of claim 1, wherein the facial skin is forehead skin, cheek skin, chin skin, and/or orbital area skin.

7. The method of claim 1, wherein the composition is an emulsion.

8. The method of claim 1, wherein the emulsion is an oil-in-water emulsion.

9. The method of claim 1, wherein the composition is a gel.

10. The method of claim 1, wherein the composition further comprises an effective amount of *Acmella oleracea* extract.

11. The method of claim 10, wherein the *Acmella oleracea* extract is obtained with a fluid extraction solvent mixture comprising water, ethanol, and 1,3 propanediol.

12. The method of claim 1, wherein the composition comprises 0.00001 to 10% w/w of *Acmella oleracea* extract.

13. The method of claim 10, wherein the *Acmella oleracea* extract is capable of reducing an influx of calcium in the facial muscle and reduces the occurrence of an action potential in the facial muscle, and/or the *Acmella oleracea* extract is capable of stimulating collagen production and laminin production in the skin.

14. The method of claim 10, wherein the *Acmella oleracea* extract stimulates collagen production and laminin production in the skin.

15. The method of claim 1, wherein the composition reduces influx of calcium levels in myotubes.

16. The method of claim 1, wherein the composition is a lotion.

* * * * *